US006840909B2

(12) United States Patent
Gatto

(10) Patent No.: US 6,840,909 B2
(45) Date of Patent: Jan. 11, 2005

(54) APPARATUS AND METHOD FOR INTRADUCTAL CYTOLOGY

(75) Inventor: Dominick L. Gatto, Branford, CT (US)

(73) Assignee: Acueity, Inc., Palo Alto, CA (US)

( * ) Notice: Subject to any disclaimer, the term of this patent is extended or adjusted under 35 U.S.C. 154(b) by 292 days.

(21) Appl. No.: 10/104,016

(22) Filed: Mar. 25, 2002

(65) Prior Publication Data
US 2003/0181823 A1 Sep. 25, 2003

(51) Int. Cl.[7] .............................................. A61B 10/00
(52) U.S. Cl. ...................... 600/562; 600/563; 600/570; 600/128; 600/156; 604/27
(58) Field of Search ................... 600/562–566, 600/570, 571, 573, 108, 114, 128, 130, 153, 156, 158, 159, 182; 604/19, 27, 35

(56) References Cited

U.S. PATENT DOCUMENTS

| 3,989,033 A | | 11/1976 | Halpern et al. | |
| 4,522,206 A | | 6/1985 | Whipple et al. | |
| 4,589,404 A | * | 5/1986 | Barath et al. ............... | 600/108 |
| 4,651,753 A | | 3/1987 | Lifton | |
| 5,107,513 A | | 4/1992 | Sagie et al. | |
| 5,147,354 A | | 9/1992 | Boutacoff et al. | |
| 5,171,255 A | | 12/1992 | Rydell | |
| 5,538,008 A | | 7/1996 | Crowe | |
| 5,542,432 A | | 8/1996 | Slater et al. | |
| 5,842,971 A | * | 12/1998 | Yoon ........................... | 600/101 |
| 6,059,734 A | * | 5/2000 | Yoon ........................... | 600/565 |
| 6,221,622 B1 | * | 4/2001 | Love .......................... | 435/7.23 |
| 6,500,114 B1 | * | 12/2002 | Petitto et al. ............... | 600/156 |
| 2003/0055315 A1 | * | 3/2003 | Gatto et al. ................. | 600/114 |

* cited by examiner

Primary Examiner—Charles Marmor
(74) Attorney, Agent, or Firm—Olson & Hierl, Ltd.

(57) ABSTRACT

The invention is directed toward a micro-endoscope assembly for the removal of tissue and cells from breast ducts comprising a cylindrical guide tube with a beveled distal end defining an internal cylindrical passageway and a first smaller cylindrical tube eccentrically formed in the cylindrical passageway of a smaller diameter than the tube internal cylindrical passageway and adapted to receive and guide an endoscope with a handle assembly wherein the smaller cylindrical tube together with an inner wall surface of the cylindrical guide tube forms a second passageway. A second conduit of a smaller diameter than the smaller cylindrical tube is mounted in the second passageway to divide the second passageway into two separate divided sections and is of sufficient diameter to receive a laser fiber and a micro-endoscope is mounted in the smaller cylindrical tube and a laser is mounted in the second cylindrical tube in the second passageway. The assembly is inserted into a mammary duct and the interior of the duct is viewed until an abnormality is determined in the duct. The tissue and cells from the abnormality area are dislodged, irrigated and aspirated through a suction channel to a removable collection device.

7 Claims, 3 Drawing Sheets

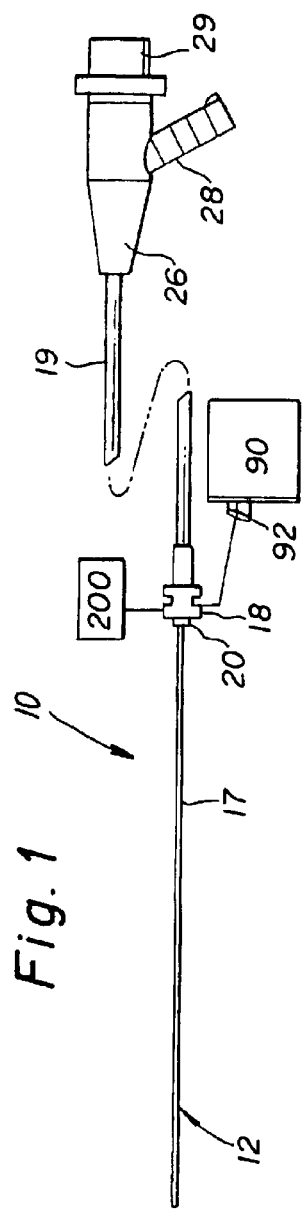
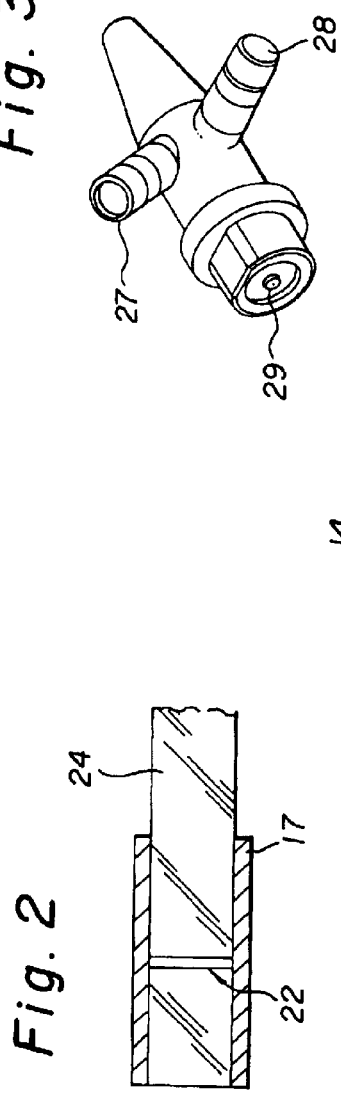
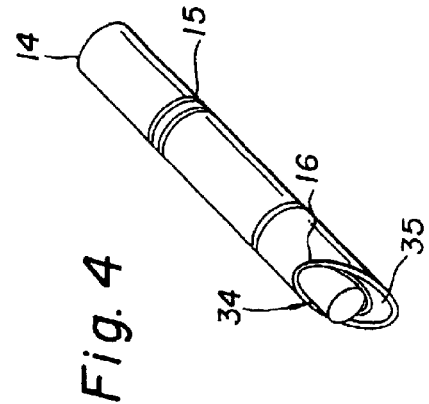

APPARATUS AND METHOD FOR INTRADUCTAL CYTOLOGY

RELATED APPLICATION

There are no related applications.

FIELD OF INVENTION

The present invention is generally directed toward the detection of breast cancer and more specifically toward the detection and collection of cancer and/or abnormal growth tissue and cells in the mammary breast ducts of women.

BACKGROUND OF THE INVENTION

A leading disease incurred by women is breast cancer. Breast cancer is the second leading cause of death for women of all ages and the leading cause of death for women aged 25–55. Approximately one in eight women will incur breast cancer in their lifetimes. The current medical standard for determining breast cancer in women is mammography. However mammography fails to detect up to 20% of breast cancers in women over 50 and up to 40% of breast cancers in younger women. Breast cancer grows slowly but under current techniques such as mammography the average detection is only on cancer growths which have been growing over seven years at which time the growth size of the cancer generally ranges between 1 and 2 cm. Almost 90% of all breast cancer originates in the mammary ducts, where it grows slowly in its initial stages.

After detection breast cancer is generally treatable in three ways: surgery, radiation and chemotherapy. Surgery and radiation, of course, have risks and disadvantages well known to those of skill in the art. Chemotherapy also can be particularly disadvantageous as, for example, when the drugs involved cause sickness to the patient when they enter the blood stream.

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome generally includes a long flexible coil having a pair of opposed jaws at the distal end and manual actuation means at the proximal end which opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site. While viewing the biopsy site through the fiber optics of the endoscope, the surgeon positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

A biopsy tissue sampling procedure often requires the taking of several tissue samples either from the same or from different biopsy sites. Unfortunately, most bioptomes are limited to large areas of entry and to taking a single tissue sample, after which the device must be withdrawn from the endoscope and the tissue collected before the device can be used again to take a second tissue sample.

Attempts have been made to provide an instrument which will allow the taking of tissue samples within small duct areas. A simple double barrel catheter with adjacent lumens is disclosed in U.S. Pat. No. 6,221,622 with one of the lumens being used to irrigate the milk duct of a breast and the other lumen being used to aspirate the fluid which has entered the duct allowing a continuous flow of saline through the duct which hopefully carries enough cells and tissues for a biopsy. Problems in the use of such an instrument include the small size required by the narrow small diameter lumens which can be blocked or limit the flow of fluid back through the aspiration lumen and thus preclude significant tissue collection or cause duct collapse. While the '622 Patent shows a small lumen size the size problem is magnified with the other existing prior art if the same were to be applied to breast ducts and the endoscope is to be used with mammary duct inspection because of the small size and thin cell walls of the mammary ducts.

Thus almost all known multiple sample biopsy instruments are precluded from use with an endoscope because of their size and rigidity. These include the "punch and suction type" instruments disclosed in U.S. Pat. No. 3,989,033 and U.S. Pat. No. 4,522,206. Both of these devices have a hollow tube with a punch at the distal end and a vacuum source coupled to the proximal end. A tissue sample is cut with the punch and suctioned away from the biopsy site through the hollow tube. It is generally recognized, however, that dry suctioning tissue samples (i.e., without the use of an irrigating fluid) through a long narrow flexible bioptome is exceptionally difficult.

The present device provides multiple sampling ability to an instrument which must traverse the narrow lumen of an endoscope or cannula housing an endoscope which in turn must traverse the small diameter of a breast duct. Numerous examples of prior art exist which are able to operate in a larger area such as U.S. Pat. No. 4,651,753 which discloses a rigid cylindrical member attached to the distal end of a first flexible tube. The cylindrical member has a lateral opening and a concentric cylindrical knife blade is slidably mounted within the cylindrical member. A second flexible tube, concentric to the first tube is coupled to the knife blade for moving the knife blade relative to the lateral opening in the cylindrical member. A third flexible tube having a plunger tip is mounted within the second flexible tube and a vacuum source (a syringe) is coupled to the proximal end of the third tube. A tissue sample is taken by bringing the lateral opening of the cylindrical member upon the biopsy site, applying vacuum with the syringe to draw tissue into the lateral opening, and pushing the second flexible tube forward to move the knife blade across the lateral opening. A tissue sample is thereby cut and trapped inside the cylindrical knife within the cylindrical member. The third flexible tube is then pushed forward moving its plunger end against the tissue sample and pushing it forward into a cylindrical storage space at the distal end of the cylindrical member. Approximately six samples can be stored in the cylindrical member, after which the instrument is withdrawn from the endoscope. A distal plug on the cylindrical member is removed and the six samples are collected by pushing the third tube so that its plunger end ejects the samples.

It can thus be seen that the preferred mode of operation of virtually all existing endoscopic tools currently being used is that a gripping action at the distal end of the instrument is effected by a similar action at the proximal end of the instrument. Another endoscopic multiple sample biopsy device is disclosed in U.S. Pat. No. 5,171,255 which discloses a flexible endoscopic instrument with a knife-sharp cutting cylinder at its distal end. A coaxial anvil is coupled to a pull wire and is actuated in the same manner as conventional biopsy forceps. When the anvil is drawn into the cylinder, tissue located between the anvil and the cylinder is cut and pushed into a storage space within the cylinder. Several samples may be taken and held in the storage space before the device is withdrawn from the endoscope. Traditional biopsy forceps provide jaws which can grasp tissue frontally or laterally. Even as such, it is difficult to position the jaws about the tissue to be sampled. Lateral sampling is even more difficult.

A traditional form of biopsy is disclosed in U.S. Pat. No. 5,542,432 which shows an endoscopic multiple sample biopsy forceps having a jaw assembly which includes a pair of opposed toothed jaw cups each of which is coupled by a resilient arm to a base member. The base member of the jaw assembly is mounted inside a cylinder and axial movement of one of the jaw assembly and cylinder relative to the other draws the arms of the jaws into the cylinder or moves the cylinder over the arms of the jaws to bring the jaw cups together in a biting action. The arms of the jaws effectively form a storage chamber which extends proximally from the lower jaw cup and prevents accumulated biopsy samples from being squeezed laterally out from between the jaws during repeated opening and closing of the jaws and the lower jaw cup enhances movement of the biopsy samples into the storage chamber. The device can hold up to four samples before it must be retrieved out of the endoscope. However, in some biopsy procedures it is sometimes desirous to retrieve more. In addition, it has been found that samples within the chamber can stick together and make determinations of which sample came from which biopsy site somewhat difficult.

U.S. Pat. No. 5,538,008 discloses a multiple sample bioptome which purports to take several samples and transfers each sample by water pressure through a duct to the proximal end of the instrument, where each sample can be individually retrieved. The device includes a plastic jaw set biased in an open position and coupled to the distal end of an elongate tube, up to seven feet long. The tube defines a duct. A sleeve extends over the tube and a water flow passage is provided between the tube and the sleeve. An aperture is provided in the tube to permit the water flow passage to meet the duct at the distal end of the tube. Withdrawing the tube into the sleeve is disclosed to force the jaws closed and enable a sample to be cut from tissue and lodge in the duct. The water flow passage is disclosed to enable water to flow under pressure from the proximal end of passage to the distal end of the passage, through the aperture and into the distal end of the duct and to be aspirated to the proximal end of the duct, thereby transferring with it any sample contained in the duct to the proximal end where the sample can be retrieved.

Generally in the field of surgery, mechanical cutters utilizing a reciprocal or rotating cutting element have been used to sever tissue of a patient. Cutting devices that use light energy to cut tissue are also well known in the art. Electro surgical devices for tissue excision or cauterization similarly have a long medical history. Such instruments have encountered numerous problems due to their one dimensional capabilities and have failed to meet many of the needs of a surgeon performing a surgical procedure.

While some lasers are effective coagulators and cutters, certain other types of lasers, $CO_2$ lasers for example, are effective at cutting tissue but are not good coagulators. Certain lasers are good coagulators but are poor tissue cutters. The YAG laser, for example, is sometimes used as a coagulator but is not considered to be a good tissue cutter.

The ablation of tissue in various other regions of the body has been previously studied. U.S. Pat. No. 5,107,513 describes the general use of three types of lasers. Carbon dioxide ($CO_2$) laser radiation is intensely absorbed by water and thus acts as a surgical knife and vaporizer, its penetration depth in tissue being 0.03 mm. Argon lasers are minimally absorbed by water but intensely absorbed by hemoglobin and penetrate 1 to 2 mm in most tissue. These lasers are especially useful in coagulating bleeding points in small superficial vessels. Neodymium-Yttrium-Aluminum-Garnet (Nd:YAG) lasers are poorly absorbed by both water and hemoglobin. These lasers are able to penetrate large volumes of tissue, blood clots and coagulate large bleeding vessels. A Holmium laser with a 2100 nm wavelength has good cutting capabilities and its coagulating properties are similar to those of the Nd:YAG laser, penetrating to about 0.4 mm for most tissue. The Holmium laser was noted to be useful for the following applications: (1) in the gastrointestinal tract for bleeding ulcers, excision of lesions, recanalization of obstruction and arresting of massive bleeding; (2) in general surgery for cutting without bleeding; (3) in urology for treatment of the bladder; (4) for creation of vascular anastomoses; (5) for aneurysms, patent ducts, varicose veins and hemangiomas to generate thrombosis; (6) for dissolution of gall bladder stones by insertion of a fiber optic into the bile duct; (7) for destruction of tumors in the bronchial tree; (8) in gynecology for fallopian tube shrinkage and removal of polyps, benign tumors and septum and for ablation of the endometrium for menorrhagia; (9) in cardiac surgery for treatment of obstructed valves; and (10) in neurosurgery for removal of solid as well as vascular tumors.

U.S. Pat. No. 5,147,354 describes the use of a mid-infrared laser endoscope for performing arthroscopy. Holmium:YAG and Holmium:YLF lasers with wavelengths in the 1800 to 2200 nm range are used for producing laser ablations in a fluid field. The radiation is said to be easily transmitted through a conventional quartz optical fiber.

Thus, there is a need in the art for new and better micro-cannula/endoscope assemblies and methods for using same that can be used to directly visualize the mammary ducts of a breast where visualization is by means of endoscopic devices, direct visualization (as opposed to creation of photographic images) and offers the additional advantage that the equipment required is comparatively simple to use and is less expensive than the equipment required to create photographic displays from such images. In addition, there is a need in the art for a method of identifying diseased or abnormal tissue during surgical procedures so that immediate resection or biopsy of the identified tissue can be performed without the necessitating the use of additional instrumentation.

SUMMARY OF THE INVENTION

The present invention is directed toward the detection, sample collection and/or treatment of abnormal growths and cancer located in the mammary ducts of women's breasts which in the present invention is when the cancer is typically between two and three years old with a size of about 0.2 mm. This is over 50 times more sensitive than a standard mammogram. According to a further aspect of the invention, a method is provided for retrieving one or more biopsy tissue sample(s) using a micro-endoscope assembly having irrigation and aspiration capabilities. The micro-endoscope assembly includes a proximal actuation handle, an elongate flexible member extending from the proximal actuation handle and having an irrigation conduit, a distal assembly located at the distal end of the biopsy instrument, and a fluid pressure device in fluid connection with the irrigation conduit.

The method comprises the steps of: inserting the distal end of the micro-endoscope assembly into a lactiferous duct of the breast of a woman patient; viewing the inside of the duct as the distal end of the endoscope travels along the duct until a tissue abnormality is viewed; positioning the distal assembly proximate to a tissue to be sampled; detaching a tissue and/or cell sample from the tissue abnormality site using the beveled end of the cannula of the micro-endoscope assembly; introducing irrigation and subsequently a negative pressure through the fluid pressure device and the irrigation conduit while transporting fluid through the irrigation conduit to flush the tissue sample through an aspiration conduit from the distal end to the proximal end of the endoscope into a reservoir and member container therein and recovering the tissue sample.

It is thus an object of the invention to provide a micro-endoscope assembly which can view the interior of a lactiferous duct to ascertain abnormalities and obtain tissue and cell samples from the site.

It is an object of the invention to utilize a micro-cannula with an eccentrically mounted endoscope conduit to provide maximum room in the micro-cannula for other additional functions including aspiration, irrigation and laser treatment.

It is yet another object of the micro-endoscope assembly invention to provide for the extraction of intraductal tissue for more reliable diagnosis with more precision and less trauma than conventional biopsy procedures.

It is also an object of the micro-endoscope assembly invention to provide for micro-endoscopic screening of defined groups of patients at high risk for breast cancer.

It is an additional object of the micro-endoscope assembly invention to obtain direct real-time intraductal images allowing detection of cancerous and precancerous lesions and growths as small as 0.2 mm.

It is an still additional object of the micro-endoscope assembly invention to extract tissue and cell samples for further diagnosis.

It is also an object of the micro-endoscope assembly invention to create an endoscope assembly which can be easily handled by the physician.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

BRIEF DESCRIPTION OF THE DRAWINGS

FIG. 1 is an exploded side elevational view of the endoscope used in the present invention;

FIG. 2 is an enlarged partial cross section of the lens end of the endoscope in FIG. 1;

FIG. 3 is a perspective orientated view of the back end of the endoscope showing a light post and laser post;

FIG. 4 is a perspective view of a portion of the front end of the micro-endoscope assembly;

DETAILED DESCRIPTION OF THE INVENTION

Figure 5:
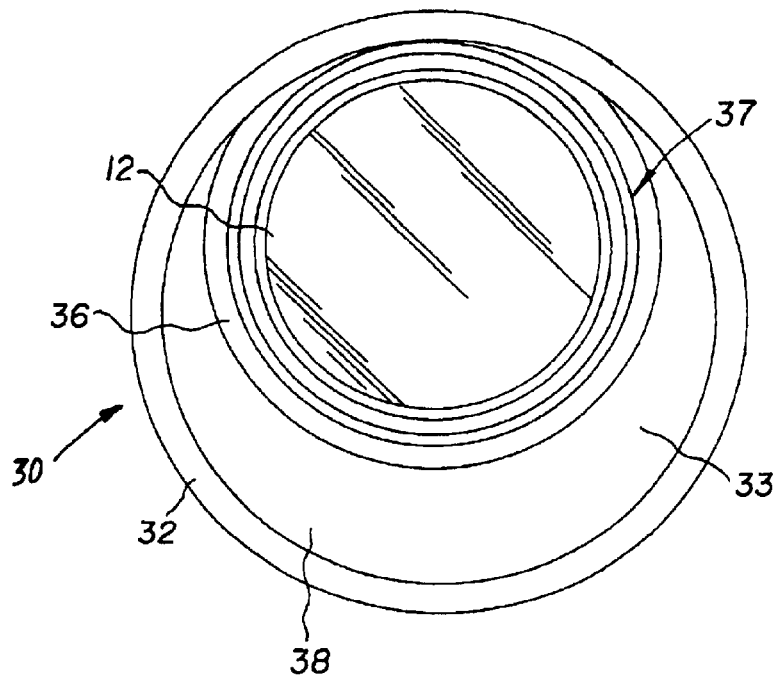
FIG. 5 is an enlarged elevational view of the front end of the micro-endoscope shown in FIG. 4.

The present invention is directed towards a micro-endoscope assembly 10 which can be used and inserted into the lactiferous ducts of the breast of a woman patient and a method for intraductal cytology. The lactiferous ducts generally range in number from about six to about twelve in women and lead from areas of the breast to the nipple where they are in parallel vertical orientation with each other. The ducts have a very thin cell wall ranging from 3 to 4 cells in thickness and are resilient. The ducts have a smooth inner surface and white color which resemble visually the interior of a standard PVC pipe.

The best mode and preferred embodiment of the invention is shown in FIGS. 1–5. The micro assembly 10 consists of tube or guide cannula 14 which seats and guides the endoscope 12. The cannula 14 has an outer cylindrical wall 16 which defines an internal passageway which runs along its length to seat and guide the endoscope 12. Cannula tube 14 may be a rigid steel tube ranging from 5–20 cm long having an outer diameter ranging from 0.5 mm to approximately 1.2 mm or alternatively may be a semi-rigid tube made of flexible or transparent plastic, or some other suitable material, and having the same or a longer length. The exterior of the cannula is marked with marking indicia 15 as seen in FIG. 4 so that the depth of penetration of the micro-endoscope assembly into the duct can be noted. The marking indicia can be in the form of rings of opaque, translucent or light reacting material or any other suitable geometry which is easily visible to the surgeon's eye. The marking indicia can be printed onto the outer surface of the cannula or imbedded in the cannula structure material. Various cannula are envisioned to be interchangeable with the endoscope 12 by unscrewing one guide cannula from the endoscope front hub 18 and its associated connector member 20 and screwing one another onto the connector member. The hub member 18 has ports which are fluidly connected to a vacuum source 90 with a cell collection reservoir 92 containing a tissue and cell collection member (not shown), the reservoir 92 being in fluid communication with an aspiration pump 200.

The endoscope 12 is provided with tube body 17 formed with objective lens 22 at its distal end and image guide 24 as is more clearly shown in FIG. 2. The endoscope 12 has a proximal end in the form of a back member 26 having a light post 27, a laser post 28 and a video port 29 as seen in FIG. 3.

The preferred cannula embodiment 30 as shown in FIG. 5 has a cylindrical outer cannula or sheath 32 formed with a beveled distal end 34 as shown in FIG. 4 forming a shovel type nose 35. The inner wall of sheath 32 defines a cylindrical inner channel 33 which has an inner cylindrical tube 36 eccentrically mounted thereon. The tube 36 defines the endoscope channel 37 and holds endoscope 12. The inner cylindrical tube 36 is eccentrically mounted in cylindrical inner channel 33 to the wall of the cannula sheath 32 and its outer surface together with the inner surface of the sheath or tube 32 to define a moon shaped channel 38 which acts as a biopsy channel providing irrigation and aspiration. The irrigation/aspiration channel 38 can also be used as a port through which a laser, such as an Eximer laser, could be utilized. In that situation, the laser is inserted through the multiple purpose channel 38 until it reaches the patient's duct area containing cells and/or tissue showing abnormal characteristics.

Figure 6:
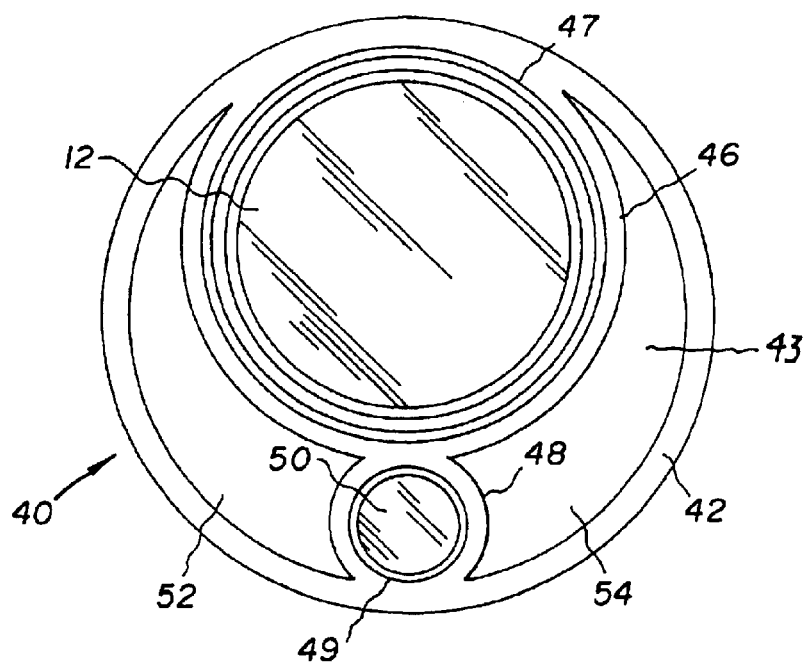
FIG. 6 is an alternate embodiment of the micro-endoscope assembly invention.

An alternate embodiment of the cannula 40 is shown in cross section in FIG. 6. This embodiment has a cylindrical outer cannula or sheath 42 which defines a cylindrical inner channel 43 in which an inner cylindrical tube 46 is eccentrically mounted to the wall of sheath 42. The cylindrical tube 46 defines the endoscope channel conduit 47 to hold the endoscope 12. A second smaller cylindrical tube 48 is eccentrically mounted in channel 43 adjacent to and integral with a portion of the wall of tube 46 and a wall of the cannula 42 to form a laser fiber channel 49 which holds laser fiber 50. The cylindrical tube structure 46 divides the moon shaped channel up into two separated segments 52 and 54 which serve as the irrigation and aspiration channels for the assembly or for a channel for bundled illumination fibers and/or a mechanical tissue scraping or cutting device. These segmented channels allow the physician to irrigate and aspirate the area of the duct containing abnormal cells or structure and deposit the same onto a sample tissue and cell container in the form of a foam disk or porous substrate to provide a cytology sample of the duct area for examination. The aspiration conduit is of a diameter sufficient to retrieve biopsy samples from the distal end of the instrument.

Figure 7:
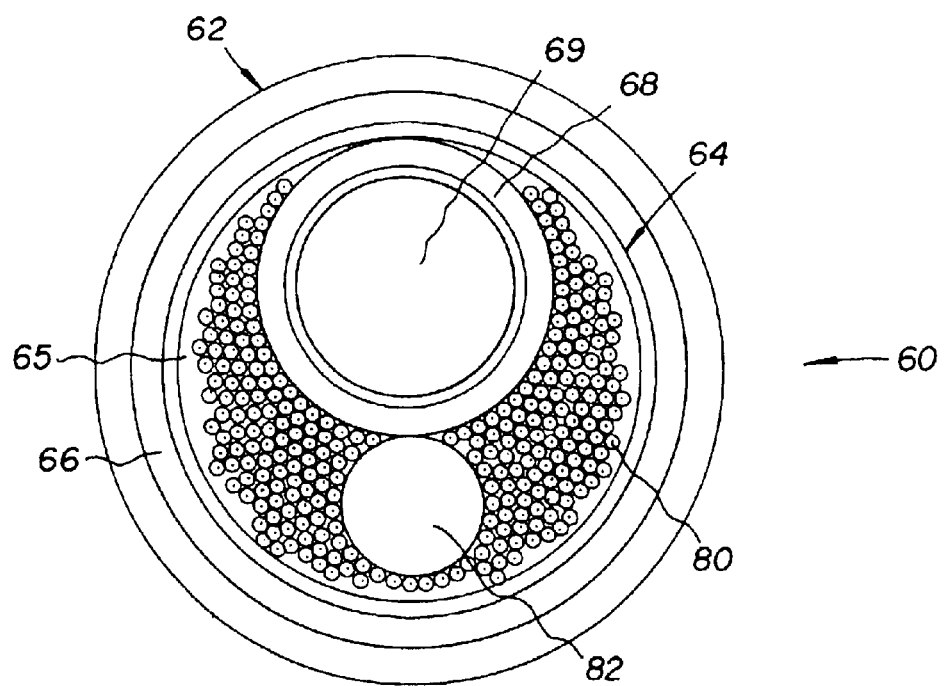
FIG. 7 is another embodiment of a micro-endoscope.

Another embodiment as shown in cross section in FIG. 7 is a micro-endoscope 60 which is constructed with an outer cannula or sheath 62 and an inner cannula or sheath 64 positioned within the chamber of cannula 62 to define an irrigation/aspiration channel 66 defined by the inner wall surface of cannula 62 and the outer wall surface of inner cannular 64. The inner wall of cannula 64 defines a cylindrical inner chamber 65 which has an inner cylindrical tube 68 mounted therein. The tube 68 defines the image guide 69 and holds the lens. The inner cylindrical tube 68 is eccentrically mounted in cylindrical chamber 65 adjacent the inner wall of the cannula 64 and is substantially surrounded by a bundle of individual light fibers 80 and is adjacent to a laser fiber 82 which is positioned adjacent to outer wall of the inner cannula 64 within the bundle of laser fibers 82.

FIG. 1 also shows the endoscope 12 with the lens tube 17 and tube portion 19 coupled between hub 18 and back end 26. Tube 19 includes a passageway in it's interior capable of holding fiber optic strands and/or illumination strands. Such strands run from video port 29, through tube portion 19 into hub 18. The strands run through hub 18 into the inner passageway of tube portion 17 though or outside of the working channel, as described in more detail below. These strands provide both a light source to the area of the the duct in which cytology is to be taken. The back end 26 is formed with a light source post connector 27 and laser post connector 28. The tube portion 14 which has an outer diameter of approximately 1.2 mm has a working channel, a plurality of light fibers 80 and a lens 22. The light fibers 80 run the length of the guide tube 17 and provide light to the areas of interest. The light fibers are commercially available. The tube cannula 14 can alternately carry the light fibers or have them molded in the tube material. The lens 22 also runs longitudinally down inner passage of guide tube 17. The laser fiber 50, 82 transmits the laser energy out the distal end of the endoscope via the contact laser tip to the surgical site. Suitable lasers which can be used with the invention are manufactured by Surgical Laser Technology, Inc.

Because the cannula tube is of such a small outer diameter, the physician can manipulate the tube from the proximal end in order to scrape cells free of the tissue by engaging the same with the beveled end 34 and shovel tip 35. The physician can then irrigate the location by ejecting saline water under pressure through the irrigation channel through the operation of the pump 200 which can be a syringe. This causes the saline water injected into the patient to mix with and carry the scraped biopsy cells and tissue. Such water and cells can be withdrawn by a vacumn source 90 and deposited on the tissue collection strata held in reservoir 92. The tissue collection strata can take the form of a small disk shaped device having layered porous foam which fits in a reservoir 92 of the aspiration channel of the micro-endoscope assembly. The disk has several layers of foam having different porosity and density. One of the layers traps tissue particles and another layer traps cells. The disk can be removed after each biopsy usage and marked in a container as to the duct from which it was removed and the depth of length of duct where it came from.

The endoscope 12 is used in conjunction with a video monitor and prismatic screen (not shown). The video port 29 is coupled to a video camera which is in turn coupled to a video monitor as is well known in the art and has an attached prismatic screen manufactured by Acueity Inc. The video camera may be of many different commercially available models, although CCD cameras are particularly useful in this type of application. Specifically, a Panasonic GS99-NTSC medical video endoscopy camera, from Matsushita Electric Corporation of America, has been found to be useful. Moreover, it has been found that in such a camera ¼ inch CCD chip is more advantageous than a ½ inch CCD chip, because it provides an image with smaller pixels. Such chips are included in CCD cameras and also are commercially available from many sources such as, for example, the Sony Corporation of America. The video monitor may be any of a number of commercially available video monitors.

It is not necessary to include a prismatic screen to use the endoscope of the present invention. However, the use of such a screen is advantageous because, as described above, the screen provides an image with increased clarity and perception of depth by causing the brain of the viewer to interpret depth cues present in the image. This increased perception of depth is particularly advantageous in medical procedures like those that employ endoscopes because of the small dimensions involved and the limited lighting available in the interior of a patient's body.

In operation the micro-endoscope assembly 10 using the rigid guide tube 14 is placed in a lactiferous duct in the patients breast after the nipple has been numbed The physician can view the interior of the duct, which has a white smooth surface, as the endoscope passes on its way through the duct to the area of interest which has an abnormal appearance and is found by watching the screen attached to video monitor. Once the duct area of interest is reached, the physician can manipulate the biopsy tube end 35 to dislodge the tissue and cells in the tissue area and retrieve cells and tissue from that area by irrigating the area and aspirating the fluid and tissue/cells to a collection site where the same are deposited on an easily removable cytology disc which traps cells and tissue or are poured into a sterilized plastic container, and taken to pathology for diagnostic testing. If the lens of the endoscope 10 is needed to be cleared of blood or tissue the aspiration channel is used as an irrigation channel by applying a liquid under pressure through the use of a syringe attached to the irrigation port.

The principles, embodiments and modes of operation of the present invention have been described in the foregoing specification. The invention that is sought to be protected herein, however, is not to be considered as limited to the particular forms disclosed, since these are to be regarded as illustrative rather than restrictive. Variations and changes may be made by those skilled in the art without departing from the spirit and scope of the invention. For example, the present invention is not limited to the particular dimensions or uses described, except as explicitly defined in the claims. Instead, the embodiments described here should be regarded as illustrative rather than restrictive. Variations and changes may be made by others without departing from the scope of the present invention as defined by the following claims:

What I claim is:

1. A micro-endoscope assembly for the removal of tissue and cells from breast ducts comprising a cylindrical guide tube including an inner wall defining an internal cylindrical passageway, a smaller diameter cylindrical tube concentrically mounted in said cylindrical passageway to form a cylindrical space there between forming an irrigation/aspiration chamber, a light guide and lens tube eccentrically mounted in said smaller diameter cylindrical tube and adapted to receive therein a light guide and lens, a plurality of illumination fibers mounted in said smaller cylindrical tube engaging an outer wall of said light guide and lens tube holding the same in place within the smaller diameter cylindrical tube and a laser fiber mounted and received in said smaller diameter cylindrical tube between the outer wall of said light guide and lens tube and said inner wall of said cylindrical guide tube engaging the outer wall of said light guide and lens tube and surrounded by and engaging directly against said illumination fibers.

2. A micro-endoscope assembly as claimed in claim 1 wherein said irrigation/aspiration chamber is connected by a conduit to a tissue cell collection reservoir.

3. A micro-endoscope assembly as claimed in claim 1 wherein said cylindrical guide tube has marking indicia placed thereon to provide duct depth penetration measurements.

4. A micro-endoscope assembly as claimed in claim 3 wherein said cylindrical guide tube marking indicia is in the form of rings.

5. A micro-endoscope assembly as claimed in claim 1 wherein said cylindrical guide tube has a distal beveled end.

6. A micro-endoscope assembly as claimed in claim 1 wherein said cylindrical guide tube has a distal end which is shovel shaped.

7. A micro-endoscope assembly as claimed in claim 1 wherein said cylindrical guide tube has a distal end which is cylindrical.

* * * * *